United States Patent [19]

Khare

[11] 4,113,433

[45] Sep. 12, 1978

[54] RADIOIMMUNOASSAY OF HORMONES AND METABOLITES IN BLOOD SERUM AND PLASMA

[76] Inventor: Gyaneshwar Prasad Khare, 311 S. Heatherstone St., Orange, Calif. 92669

[21] Appl. No.: 640,841

[22] Filed: Dec. 15, 1975

[51] Int. Cl.$^2$ .......................................... G01R 33/16
[52] U.S. Cl. .................................. 23/230.6; 250/303; 424/1.5; 424/12
[58] Field of Search ..................... 23/230.6; 424/8, 12, 424/1, 1.5; 195/103.5; 250/303, 304

[56] References Cited

U.S. PATENT DOCUMENTS

| | | | |
|---|---|---|---|
| 3,088,875 | 5/1963 | Fisk | 424/12 |
| 3,414,383 | 12/1968 | Murphy | 23/230.6 |
| 3,853,987 | 12/1974 | Dreyer | 23/230.6 X |
| 3,928,628 | 12/1975 | Kosmiderski et al. | 424/8 X |

*Primary Examiner*—Robert M. Reese

[57] ABSTRACT

Hormones or metabolites which are capable of producing antibodies can be detected and precisely quantitated by this method. Antibodies, to various hormones or metabolites whose assay is desired, are adsorbed onto commercially available imitation or cultured pearls. These pearls coated with antibody are contacted with a buffered reaction mixture containing blood serum or plasma specimen and respective radioactive antigen. The entire reaction is allowed to proceed for a time sufficient to form antigen (radioactive or non-radioactive)-antibody complex. These complexes on the pearls are washed and the total amount of radioactivity emanating from the complex is measured. This is indicative of the extent of binding of radioactive antigen and provides an indirect correlation of the amount of non-radioactive antigen present in the serum or plasma sample.

10 Claims, No Drawings

RADIOIMMUNOASSAY OF HORMONES AND METABOLITES IN BLOOD SERUM AND PLASMA

BACKGROUND OF THE INVENTION

This invention relates to a concept that antibody to an antigen can be coupled to a solid material and this can be used in a test system for the detection or measurement of that particular antigen. Some of these procedures have been known for a long time but with the use of present invention and modifications therein, complete automation of the technique with greater sensitivity and specificity can be achieved.

The newest trend in diagnostic procedures has been the usage of radioactive tracers. The technique of radioimmunoassay (RIA), subject of present invention, is a combination of certain radioactive and certain immunological procedures. Briefly, this radioimmunological technique consists of reacting the antibody with radioactively labeled and/or unlabeled antigen. There is a competition between the labeled and unlabeled antigen for the specific antibody. The binding of the radioactive antigen, therefore, depends on the concentration of non-radioactive antigen present during the reaction. This complex is then separated by a variety of precedures such as precipitation with a salt, precipitation by antiantibodies or simple washing. Some of these procedures involve special handling or centrifugation of the reactants prior to final analysis. The sensitivity and specificity are considerably affected because of these additional manipulations.

Therefore, the present invention is designed to provide an improved process by which various hormones or metabolites could be detected and quantitated.

Another object of the present invention is to provide a simple, modified methodology in solid phase radioimmunoassay which is sensitive and has greater specificity.

DESCRIPTION OF THE PREFERRED EMBODIMENTS

The present invention provides an improved solid phase radioimmunoassay that is simple and capable of quantitating the concentration of various hormones or metabolites in the serum or plasma. During the course of this reaction an antigen-antibody complex is formed.

Several methods are available to prepare antibody against various hormones and metabolites. The choice animals for antibody production are rabbits and goats although antibodies produced in other laboratory or domestic animals could also be used. The blood is removed from such hyperimmunized animals and serum collected.

The antibody containing serum is used for the preparation of antibody coating solution. One improvement lies in the choice of material used for coating the antibody. The solid phase radioimmunoassay described in the past has utilized the interior of a tube for antibody coating (Kevin Catt, et al., *Journal of Biochemistry*, Volume 100, Pages 31c–33c, 1966 and *Science*, Volume 158, Page 1570, 1967). However, coating of interior of a tube lacks reproducibility, sensitivity and specificity. An improvement in this procedure is achieved by utilizing commercially available imitation or cultured pearls for antibody adsorption. The usage of pearls not only facilitates antibody adsorption but also increases the specificity and thereby providing a better quantitation of the hormones or metabolites since these pearls could be thoroughly washed to remove the unbound radioactive antigen. The size and the shape of these pearls could vary. However, spherical pearls of sizes ranging from 3 mm to 8 mm are preferred. The number of pearls in one single reaction could also vary. However, one pearl of the size of 6 mm is preferred in a single reaction. These antibody coated pearls provide a solid matrix for their radioimmunoassay system. The following examples will illustrate the details of the procedure:

EXAMPLE I

The pearls are coated at 4° C to about 45° C for periods ranging from 30 minutes to 24 hours by contacting them with a buffered solution containing optimum levels of desired antibody serum. Either of the two following solutions can be used:

SOLUTION A: An aqueous buffer consisting of 0.02 to about 0.08 M Tris-(hydroxy methyl) amino methane-HCl at pH 7.4 to about 8.8 and calcium chloride at a concentration of 10 to 100 $\mu$g/ml. The antibody serum is diluted to the optimum levels in this solution. The entire solution could be sterilized by filtration through 0.2 micron sterile filter. A typical suitable buffer useful in the process is 0.02 M Tris-HCl, pH 7.4 containing 100 $\mu$g/ml of calcium chloride.

SOLUTION B: An aqueous buffer consisting of 0.005 to 0.08 M phosphate at pH 7.1 to 8.8 and 0.15 M sodium chloride (phosphate buffered saline). The antibody serum is diluted to the optimum levels in this buffer. The entire solution could be sterilized by filtration through 0.02 micron sterile filter. A typical suitable buffer is 0.02 M phosphate at pH 7.4 and 0.15 M sodium chloride.

Sodium azide at 0.02% to about 0.06% levels is used as a preservative in either solution.

The pearls are then coated with this solution. Approximately 17 ml ± 0.5 ml of buffered antibody solution is sufficient for 100 pearls. At the end of the coating period the solution is removed and the pearls are washed with either Tris-HCl buffer (0.02 to about 0.08 M, pH 7.4 to about 8.8) or phosphate-buffered (0.005 to about 0.08 M pH 7.1 to about 8.8) saline each containing sodium azide at concentrations 0.02% to about 0.06%. The remaining moisture content from the pearls is removed by lyophilization to a moisture content of less than 1.0%. The lyophilized pearls can be stored up to a period of six months at temperatures between −80° C to about 8° C.

EXAMPLE II

Examples of hormones that could be analyzed by this procedure are triiodothyronine ($T_3$), thyroxine ($T_4$), growth hormone, angiotensin, insulin, parathormone, thyroid stimulating hormone, aldosterone and many others of biological significance.

EXAMPLE III

Either of the following two buffers could be used as a reaction buffer.

BUFFER A: An aqueous barbital buffer 0.01 M to about 0.1 M and pH 7.1 to about 8.8. The buffer could be sterilized through 0.2 micron sterile filter. A typical suitable buffer useful in the process is 0.07 M barbital buffer at pH 8.6.

BUFFER B: An aqueous buffer consisting of 0.005 M to about 0.08 M phosphate at pH 7.1 to about 8.8 and 0.15 M sodium chloride (phosphate buffered saline). The buffer could be sterilized through 0.2 micron sterile filter. A typical suitable buffer useful in the process is 0.02 M phosphate at pH 7.4 and 0.15 M sodium chloride.

Sodium azide at 0.02% to about 0.06% levels is used as a preservative.

In the serum exists a protein, thyroxine-binding globulin (TBG) which has a relatively high affinity for the thyroid hormone. Before $T_3$ or $T_4$ is determined in an unextracted serum this interference due to serum TBG should be eliminated. ANS (8-anilino-1-naphthalene-sulfonic acid) has been successfully used to eliminate this interference (Chopra, et al., *J. Lab. Clin. Med.*, Volume 80, page 729, 1972). However, ANS was used in radioimmunoassay involving a second antibody to precipitate the bound radioactivity followed by centrifugation and washing. It is the purpose of this invention to use ANS in this solid phase radioimmunoassay system which does not involve a second antibody and additional manipulations like centrifugation. In this procedure sufficient Buffer A containing 50–400 micrograms (ug) of ANS is added per tube. A typical suitable displacement buffer for $T_3$ or $T_4$ assay consists of barbital buffer 0.07 M pH 8.6 and 200 ug. of ANS per reaction tube.

EXAMPLE IV

Concentrations of various hormones at nanogram (ng) levels (for example, $T_3$: 0 to about 400 ng/ml) are prepared usually in buffer containing 0.05% to about 2.5% of human serum albumin. Normal serum may be enriched to prepare high control standards. Standards at zero level, low level, intermediate level and high levels are frequently used during the reaction. These may be stored lyophilized and reconstituted to desired volume prior to use.

EXAMPLE V

The antigens to be used during the radioimmunoassay procedure as described in this invention could be labeled with a radioactive material. However, it is preferred to employ $^{125}I$ in the form of $Na^{125}I$. This procedure of producing a radioactively ($^{125}I$) labeled antigen is identified as iodination and is essentially a modification of the procedure of Hunter and Greenwood (Nature, Volume 194, page 495, 1962). Approximately 2 mCi of $^{125}I$ is oxidized with Choramine T and the reaction subsequently terminated by the addition of sodium metabisulfite. Potassium iodide may also be added in some instances to terminate the reaction. The hormones labeled with $^{125}I$ are separated from the low molecular weight products and iodide by gel filtration. The fractions containing the RIA reactivity are pooled, diluted as per requirements and stored at 8° C or lower. Sometimes stabilizers like crystalline bovine serum albumin (0.05 to about 4%) are used during gel filtration at the final dilution step. The radioactive antigen may be lyophilized and subsequently reconstituted to desired volume prior to use. Desired radioactive antigen may be obtained commercially.

EXAMPLE VI

The assay may be performed according to the following procedure:

Serum or plasma may be used in the assay.

Into a series of disposable culture tubes, reaction buffer is added. In case of assay for $T_3$ or $T_4$ the displacement buffer as described in Example III containing ANS is used. The size of tube or the volume of the reaction or displacement buffer are not important. However, it is preferred to use 0.5 ml of the buffer in 12 × 75 mm glass culture tubes. Properly capped tubes containing predispensed buffer can also be used in which case any evaporation of the reagent should be avoided.

Sample or standards containing increasing concentrations of unlabeled antigen is subsequently added. Standards consisting of zero, low, intermediate and high concentrations of the respective unlabeled antigen may also be used. The volume of sample or standard may vary. Usually 0.01 ml of the sample or standard is used. It is advisable to have two tubes of standards at each concentration so as to avoid the likelihood of a defective run.

A constant volume of antigen labeled with $^{125}I$ is then added. If the standards or radioactive antigen are lyophilized, they are brought to the desired volume before the start of the test. Although the volume of radioactive antigen could be varied, 0.1 ml of radioactive antigen may be preferred.

The sequence of addition of reaction buffer, sample or standards, radioactive antigen and respective antibody coated pearls could be varied to obtain optimum sensitivity. However, the reaction buffer, sample or standards, radioactive antigen and respective antibody coated pearls should be incubated at 20° C to about 45° C for a time sufficient to insure the formation of antigen-antibody complex on the pearls. Optimum reactivity is obtained at any time during the first six (6) hours of incubation depending upon the type of hormone or metabolite whose assay is desired.

At the end of the reaction the entire reaction mixture is aspirated and the pearls washed with water which may be distilled or deionized or with a suitable buffer. A suitable buffer for this purpose could be Tris-HCl (0.02 to about 0.08 M, pH 7.4 to about 8.8; or 0.005 to about 0.08 M phosphate buffered saline at pH 7.1 to about 8.8). The number of washings and the volume of wash solution is not important, only objective being to remove maximum proportions of unbound radioactive antigen without losing sensitivity or specificity. Usually two or three washings with 2.0 ml of wash solution would be sufficient. The amount of bound radioactivity on each pearl is determined using a radioisotope counter capable of counting gamma radiation. In some instances the pearls may be transferred to clean tubes prior to counting to obtain better sensitivity.

A concentration graph is prepared using the ratio between counts present on the pearls and total counts for each tube. This is done by plotting on a graph the corrected binding percentage (percent $^{125}I$ bound) and the concentration of hormone or metabolite present in the standard. This graph is used for the determination of respective hormone or metabolite present in the unknown sample.

This procedure is simple and requires less manipulation and additional ingredients like precipitation by a second antibody.

However, it is apparent that many alterations could be made in the above precedures and products without departing from the scope and concept of the invention. The description presented herein should be interpreted as illustrative and not in a limiting sense.

I claim:

1. A process for assaying hormones or metabolities comprising the following:

(a) contacting antibody specific to said hormones or said metabolites coated pearl with a mixture containing reaction buffer, a sample being assayed, and a known amount of radioactive antigen, said radioactive antigen being specific to said antibody, for a period sufficient for antigen-antibody complex formation at 20° C to about 45° C, (b) removing the mixture, (c) washing the antigen-antibody complex, (d) detecting the amount of radiation emanating from the pearl bound antigen-antibody complex, (e) and relating the measured amount of radioactivity to the presence of said hormones or said metabolites in said sample.

2. A process as set forth in claim 1 wherein more than one pearl is used.

3. A process as set forth in claim 1 wherein said reaction buffer for determination of triiodothyronine ($T_3$) and Thyroxine ($T_4$) consists of an aqueous solution of barbital buffer (0.01 M to about 0.1 M) at pH 7.1 to about 8.8 containing 8-anilino-1-naphthalenesulfonic acid or its salt.

4. A process as set forth in claim 1 wherein the hormones are triiodothyronine ($T_3$), thyroxine ($T_4$), growth hormone, aldosterone, insulin, parathormone, thyroid stimulating hormone, angiotensin or other hormones and metabolites of biological significance.

5. A process as set forth in claim 1 wherein said antigens are hormones or metabolites.

6. A process as set forth in claim 1 wherein said pearl is commercially available imitation or cultured pearl.

7. A process as set forth in claim 1 wherein the pearl is spherical.

8. In a process for assaying hormones or metabolites in a radioimmunoassay competitive binding procedure wherein antibody is coated on a substrate, the improvement comprising coating the antibody on pearl.

9. A process according to claim 8 wherein said pearl is a commercially available imitation or cultured pearl and is coated with antibody directed against any hormones or metabolites of biological significance.

10. A process according to claim 9 wherein the antibody is produced in laboratory or domestic animals.

* * * * *